United States Patent [19]

Callewaert

[11] Patent Number: 5,786,351
[45] Date of Patent: Jul. 28, 1998

[54] CLAVULANIC ACID SALTS

[75] Inventor: George Leo Callewaert, Penn, United Kingdom

[73] Assignee: Spurcourt Limited, Woodley Reading, England

[21] Appl. No.: 737,891

[22] PCT Filed: Dec. 22, 1995

[86] PCT No.: PCT/GB95/03039

§ 371 Date: Dec. 3, 1996

§ 102(e) Date: Dec. 3, 1996

[87] PCT Pub. No.: WO96/20199

PCT Pub. Date: Jul. 4, 1996

[30] Foreign Application Priority Data

Dec. 24, 1994 [GB] United Kingdom ............ 9426261

[51] Int. Cl.⁶ .................... A61K 31/395; C07D 205/12
[52] U.S. Cl. ............................ 514/210; 540/349
[58] Field of Search ............... 540/349; 514/210

[56] References Cited

U.S. PATENT DOCUMENTS

| | | | |
|---|---|---|---|
| 4,144,242 | 3/1979 | Fleming et al. | 260/307 FA |
| 4,255,332 | 3/1981 | Davies | 260/245.3 |
| 4,454,069 | 6/1984 | Cook et al. | 260/245.3 |

FOREIGN PATENT DOCUMENTS

| | | |
|---|---|---|
| 0387178 | 9/1990 | European Pat. Off. |
| 1578739 | 11/1980 | United Kingdom. |
| 2264944 | 9/1993 | United Kingdom. |

Primary Examiner—Joseph McKane
Attorney, Agent, or Firm—Kohn & Associates

[57] ABSTRACT

A di-clavulanate salt derived from clavulanic acid and a diamino ether of the formula

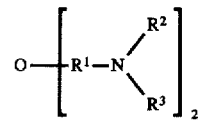

wherein $R^1$ is an alkylene group, optionally having one or more inert substituents; and each of $R^2$ and $R^3$ is a hydrogen atom or an alkyl group, optionally having one or more inert substituents, or $R^2$ and $R^3$ together complete a heterocyclic ring having four to seven carbon atoms, again optionally having one or more inert substituents. A process for preparing the clavulanic acid salt includes the steps of preparing a substantially water free solution of clavulanic acid, or a salt thereof, in an organic solvent which solution is at a maintained temperature of 0° to 15° C. and then reacting the clavulanic acid, or salt thereof, with diamino ether in the organic solvent.

17 Claims, 2 Drawing Sheets

CLAVULANIC ACID SALTS

TECHNICAL FIELD

This application is a 371 of PCT/GB95/03039 filed Dec. 22, 1995.

The present invention relates to clavulanic acid salts, their preparation and pharmaceutical compositions containing them.

BACKGROUND OF THE INVENTION

Clavulanic acid is active in antibiotic formulations because it inhibits many of the beta-lactamase enzymes, which cleave the beta-lactam ring of anti-microbial agents such as penicillins and cephalosporins. Clavulanic acid therefore improves the antibacterial actions of these antimicrobial agents. Clavulanic acid has the following formula:

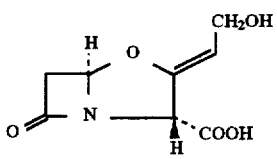

GB-A-1578739 discloses a class of amine salts of clavulanic acid, and a process for the preparation of clavulanic acid, in which the salts may be more easily formulated to give stable pharmaceutical compositions than previously described salts of clavulanic acid. Other amine salts of clavulanic acid are disclosed in, for example, GB-A-2264944; WO 93/25557 and WO 94/22873; and EP-A-0026044, EP-A-0387178 and EP-A-0562583.

Typically, such amine salts of clavulanic acid either do not crystallise or require the addition of very large amounts of a solvent, such as acetone, in order to cause crystallisation, or crystallisation in the form of fine needle shaped crystals which do not settle readily and are difficult to filter, wash and dry.

Accordingly, it is the purpose of the present invention to alleviate such difficulties, and to provide a highly stable pure salt of clavulanic acid which can be easily crystallised, or crystallise in the form of rosette shaped crystals which are easy to filter.

SUMMARY OF THE INVENTION

Thus, according to one aspect of the present invention, there is provided a di-clavulanate salt derived from clavulanic acid and a diamino ether of the formula

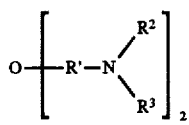

where $R^1$ is an alkylene group (the term alkylene encompassing cycloalkylene and alkyl substituted cycloalkylene), optionally having one or more inert substituents; and each of $R^2$ and $R^3$ is a hydrogen atom or an alkyl group (the term alkyl encompassing cycloalkyl and alkyl substituted cycloalkyl), optionally having one or more inert substituents, or $R^2$ and $R^3$ together complete a heterocyclic ring having 4 to 7 carbon atoms, again optionally having one or more inert substituents. When $R^2$ and $R^3$ represent alkyl groups, they each preferably have no more than 8 carbon atoms; they are preferably both the same.

It is preferred that $R^1$ contains no more than four carbon atoms, and that the $R^2$ and $R^3$ groups together contain no more than four carbon atoms. Most preferably, the diamino ether comprises bis (2-dimethylaminoethyl) ether, which advantageously forms a highly pure salt of clavulanic acid and which can be crystallised from aqueous solution by the addition of a suitable solvent such as acetone or isopropanol. It has been found that using bis (2-dimethylaminoethyl) ether, no crystalline mono clavulanate salt can be isolated, which advantageously allows a substantially homogeneous di-clavulanate to be isolated. Furthermore, the di-clavulanate salt of bis (2-methylaminoethyl) ether does not normally form a distinct solvate; this characteristic prevents any carry over of solvent, thus substantially avoiding contamination of any subsequent processing stages.

The salts according to the invention are themselves pharmaceutically acceptable and may therefore be used together with a carrier, diluent or excipient, in a pharmaceutical formulation. Alternatively, the salts may be used as intermediates for the preparation of further pharmaceutically acceptable salts of clavulanic acid, such as the potassium salt, and for pharmaceutical compositions containing such a salt.

There is further provided a process for preparing a diamino ether salt of clavulanic acid as defined above, which comprises reacting a diamino ether with clavulanic acid in an organic solvent, and isolating the resulting salt. Preferably, the organic solvent comprises an aliphatic carboxylic ester or a substantially water-immiscible aliphatic ketone; a preferred solvent is ethyl acetate. The solvent may further include a co-solvent which may, for example, be acetone, acetonitrile or tetrahydrofuran which, advantageously, improves the crystallisation characteristics and the quality of the salts obtained.

The salt thus obtained may, as indicated above, be converted to a further pharmaceutically acceptable salt of clavulanic acid, such as the potassium salt, which is then suitable for use in a pharmaceutical formulation.

There is also provided a pharmaceutical composition comprising a pharmaceutically acceptable salt of clavulanic acid produced by a process substantially as hereinbefore described, and a pharmaceutically acceptable carrier, diluent or excipient therefor. The composition preferably further comprises a beta-lactam antibiotic. Thus, the effectiveness of the beta-lactam antibiotic is maintained when administered with a pharmaceutically acceptable salt according to the invention. Typically, the antibiotic used may comprise a penicillin and/or a cephalosporin.

There is further provided a process for preparing a diamino ether salt of clavulanic acid which salt has a novel crystal habit, which process comprises preparing a substantially water-free solution of clavulanic acid, or a salt thereof, in an organic solvent which solution is kept at a temperature of between approximately 0° and 15° C., and preferably less than 10° C., and reacting with a diamino ether in the organic solvent. The process advantageously causes the diamino ether salt of clavulanic acid to crystallise substantially in the form of rosette type crystals, that is, several needle shaped crystals emanating from a single nucleation point. This is believed to be a unique property of this amine salt, which crystal habit has not been previously described for an amine salt of clavulanic acid. This crystal habit confers significant advantages in that such crystals settle rapidly in the solvent, may be filtered and washed rapidly and when dry result in a product with improved handling characteristics.

Preferably, the organic solvent comprises an aliphatic carboxylic ester or a substantially water-immiscible aliphatic ketone; a preferred solvent is ethyl acetate. The solvent may further include a co-solvent which may, for example, be acetone, acetonitrile or tetrahydrofuran which, advantageously, improves the crystallisation characteristics and the quality of the salts obtained.

BRIEF DESCRIPTION OF THE FIGURES

The invention may be more clearly understood from the following examples given by way of illustration only; in the examples, reference will be made to FIGS. 1 to 3 of the accompanying drawings, in which.

DETAILED DESCRIPTION OF THE INVENTION

Figure 1:
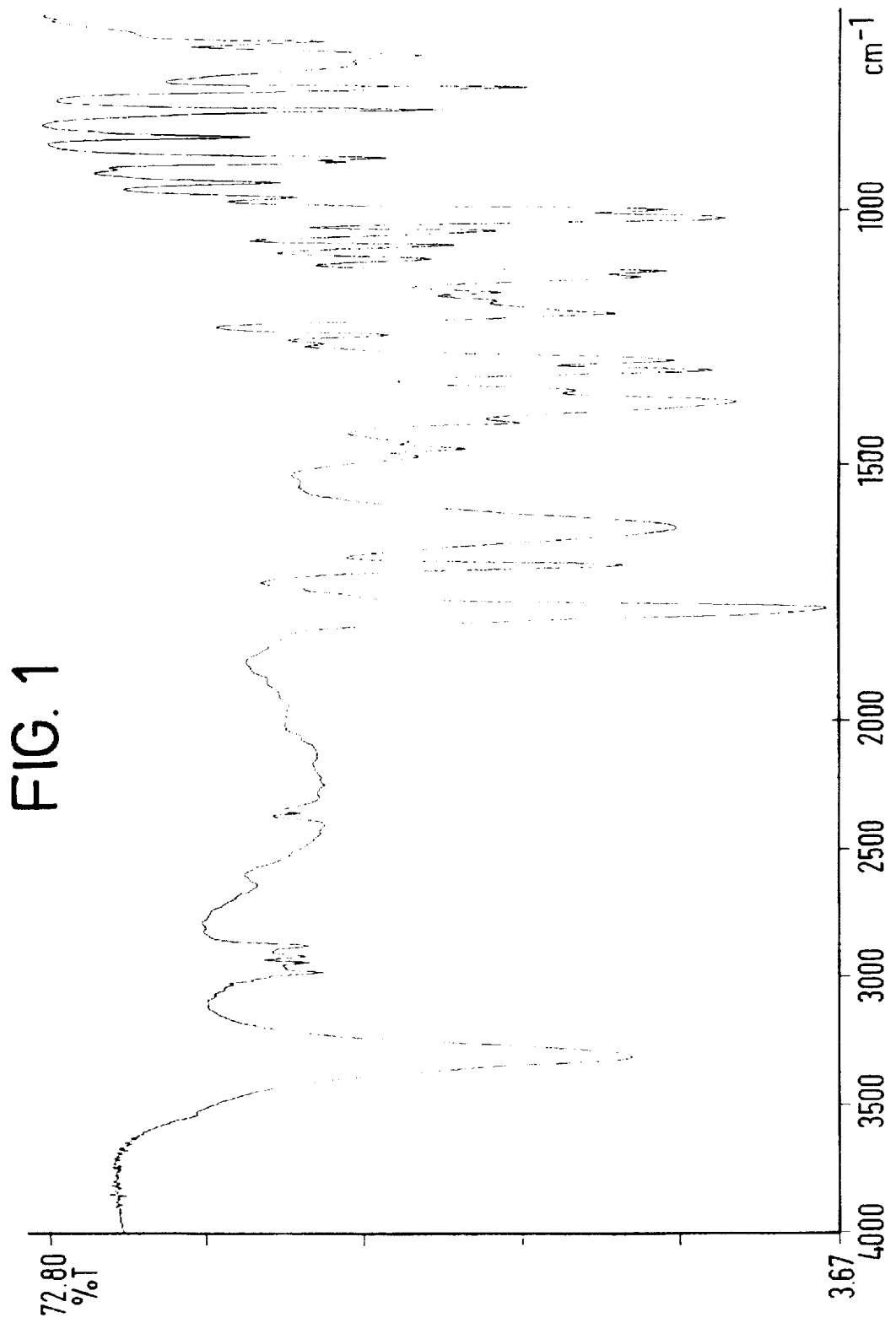
FIG. 1 is the infra-red spectrum of the crystalline product of Example 1.

There is provided a di-clavulanate salt derived from clavulanic acid and a diamino ether of the formula

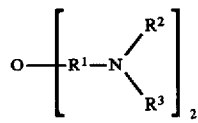

wherein $R^1$ is an alkylene group (the term alkylene encompassing cycloalkylene and alkyl substituted cycloalkylene), optionally having one or more inert substituents; and each of $R^2$ and $R^3$ is a hydrogen atom or an alkyl group (the term alkyl encompassing cycloalkyl and alkyl substituted cycloalkyl), optionally having one or more inert substituents, or $R^2$ and $R^3$ together complete a heterocyclic ring having 4 to 7 carbon atoms, again optionally having one or more inert substituents. When $R^2$ and $R^3$ represent alkyl groups, they each preferably have no more than 8 carbon atoms; they are preferably both the same.

It is preferred that $R^1$ contains no more than four carbon atoms and that the $R^2$ and $R^3$ groups together contain no more than four carbon atoms. Most preferably, the diamino ether comprises bis (2-dimethylaminoethyl) ether, which advantageously forms a highly pure salt of clavulanic acid and which can be crystallized from aqueous solution by the addition of a suitable solvent such as acetone or isopropanol. It has been found that using bis (2-dimethylaminoethyl) ether, no crystalline mono clavulanate salt can be isolated, which advantageously allows a substantially homogeneous di-clavulanate to be isolated. Furthermore, the di-clavulanate salt of bis (2-methylaminoethyl) ether does not normally form a distinct solvate; this characteristic prevents any carry over of solvent, thus substantially avoiding contamination of any subsequent processing stages.

The salts according to the invention are themselves pharmaceutically acceptable and may therefore be used together with a carrier, diluent or excipient, in a pharmaceutical formulation. Alternatively, the salts may be used as intermediates for the preparation of further pharmaceutically acceptable salts of clavulanic acid, such as the potassium salt, and for pharmaceutical compositions containing such a salt.

There is further provided a process for preparing a diamino ether salt of clavulanic acid as defined above, which comprises reacting a diamino ether with clavulanic acid in an organic solvent, and isolating the resulting salt. Preferably, the organic solvent comprises an aliphatic carboxylic ester or a substantially water-immiscible aliphatic ketone; a preferred solvent is ethyl acetate. The solvent may further include a co-solvent which may, for example, be acetone, acetonitrile or tetrahydrofuran which, advantageously, improves the crystallization characteristics and the quality of the salts obtained.

The salt thus obtained may, as indicated above, be converted to a further pharmaceutically acceptable salt of clavulanic acid, such as the potassium salt, which is then suitable for use in a pharmaceutical formulation.

There is also provided a pharmaceutical composition comprising a pharmaceutically acceptable salt of clavulanic acid produced by a process substantially as hereinbefore described, and a pharmaceutically acceptable carrier, diluent or excipient therefor. The composition preferably further comprises a beta-lactam antibiotic. Thus, the effectiveness of the beta-lactam antibiotic is maintained when administered with a pharmaceutically acceptable salt according to the invention. Typically, the antibiotic used may comprise a penicillin and/or a cephalosporin.

There is further provided a process for preparing a diamino ether salt of clavulanic acid which salt has a novel crystal habit, which process comprises preparing a substantially water-free solution of clavulanic acid, or a salt thereof, in an organic solvent which solution is kept at a temperature of between approximately 0° to 15° C., and preferably less than 10° C., and reacting with a diamino ether in the organic solvent. The process advantageously causes the diamino ether salt of clavulanic acid to crystallize substantially in the form of rosette type crystals, that is, several needle shaped crystals emanating from a single nucleation point. This is believed to be a unique property of this amine salt, which crystal habit has not been previously described for an amine salt of clavulanic acid. This crystal habit confers significant advantages in that such crystals settle rapidly in the solvent, may be filtered and washed rapidly and when dry result in a product with improved handling characteristics.

Preferably, the organic solvent comprises an aliphatic carboxylic ester or a substantially water-immiscible aliphatic ketone; preferred solvent is ethyl acetate. The solvent may further include a co-solvent which may, for example, be acetone, acetonitrile or tetrahydrofuran which, advantageously, improves the crystallization characteristics and the quality of the salts obtained.

As is well known from the scientific literature, certain amine salts of clavulanic acid have been shown to form hydrates and solvates. Generally such compounds are not well defined and are variable composition. Also, on some occasions, in order to demonstrate their existence, it has been necessary to contrive conditions which would not ordinarily apply during a process to recover and purify clavulanic acid. In any case, the formation of solvates can be a considerable nuisance because of the inevitable carry over of solvent to subsequent processing stages. The ether diamine salts of clavulanic acid do not normally appear to form solvates with the solvents commonly used in clavulanic acid extraction and purification processes. However, their existence as transient or low level intermediates in which the solvent is loosely bound cannot be totally discounted. Therefore the ether diamine salts of clavulanic acid in which there is present some small amount of solvent or water are to be considered as falling within the scope of the present invention.

EXAMPLE 1

Preparation of the di clavulanate salt of bis (2-dimethylaminoethyl) Ether

Figure 2:
FIG. 2 illustrates the shape of the crystals obtained from Example 1.

A magnesium sulfate and decolourising charcoal treated solution of clavulanic acid in ethyl acetate was prepared by known means. To 100 ml of this solution which contained 3.0% w/v clavulanic acid was added 100 ml acetone and the resulting mixture stirred at ambient temperature. There was then added slowly with continued stirring a solution of 2.0 grams of bis (2-dimethylaminoethyl) ether (available commercially as "Jeffcat ZF-20"), a trademark of Huntsman Petrochemical Corporation, 500 Huntsman Way, Salt Lake City, Utah 84108 in 8.0 ml acetone to the point where the solution became cloudy due to the formation of a fine suspension of oily droplets. A small sample of this suspension was transferred to a test tube and a slight excess of the amine was added followed by acetone to the point where the suspension cleared. After a few moments crystals were observed. This suspension of crystals was added back to the original mixture to act as a crystallisation seed and addition of the remaining solution of amine continued. Crystallisation of the mixture was completed by stirring at ambient temperature for 30 minutes and then at 0°–3° C. for a further two hours. The white crystalline product was then filtered, washed with a little acetone and dried in vacuo overnight to yield 3.5 grams of the salt (yield 83%). The shape of the crystals obtained is shown in FIG. 2, which is a photomicrograph at magnification×100 of a batch of crystals.

An analysis of the crystalline product obtained gave the following results:

|  |  | Calculated |
| --- | --- | --- |
| Carbon (% m/m) | 51.79 | 51.61 |
| Hydrogen (% m/m) | 6.85 | 6.86 |
| Nitrogen (% m/m) | 10.09 | 10.03 |
| Melting Point (°C.) 152–154° C. melted with decomposition | | |
| FT-IR shown in Figure 1 | | |

EXAMPLE 2

Figure 3:
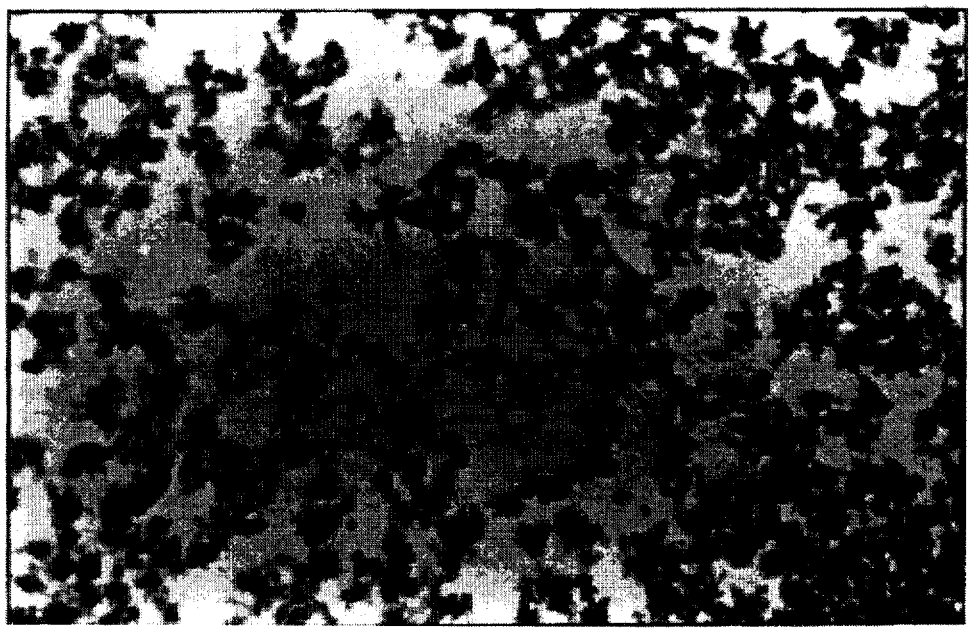
FIG. 3 illustrates the rosette-type crystals obtained from Example 2.

Preparation of the diclavulanate salt of bis(2-dimethylaminoethyl) ether in the Form of Rosette Type Crystals A decolourising charcoal treated solution of clavulanic acid (0.25% w/v clavulanic acid) in ethyl acetate was prepared conventionally. One litre of this solution was reduced in volume to 100 ml using a rotary evaporator. To this solution was added 100 ml acetone (water content less than 0.2% v/v) and the resulting mixture stirred at 5° to 10° C. There was then added rapidly 1.5 grams of bis (2-dimethylaminoethyl) ether in 6.0 ml acetone with vigorous stirring. Crystal formation was rapid and thereafter the rate of stirring was reduced to the minimum necessary. Crystallisation of the mixture was completed by stirring at 5° to 10° C. for 30 minutes and then at 0° to 3° C. for a further two hours. The white crystalline product in the form of a dense mixture of "rosette" and needle shaped crystals was then filtered, washed with a little acetone and dried in vacuo overnight to yield 2.8 grams of the salt (yield 80%). The shape of the crystals obtained is shown in FIG. 3, which is a photomicrograph at magnification×100 of a batch of crystals.

EXAMPLE 3

Preparation of the Potassium Salt of Clavulanic Acid

With stirring at ambient temperature 1.0 grams of the di clavulanate salt of bis (2-dimethylaminoethyl) ether was dissolved in 75 ml isopropanol which contained 2.2% v/v water. To this solution was added 2.5 ml of a 2N solution of potassium 2-ethyl hexanoate in isopropanol with continued stirring. After completion of this addition, the mixture was stirred at ambient temperature for 30 minutes and then at 0°–3° C. for a further two hours. The product was filtered, washed with isopropanol and acetone and dried in vacuo overnight to yield 0.64 grams of the salt (yield 75%).

What is claimed is:

1. A di-clavulanate salt prepared from clavulanic acid and a diamino ether of the formula

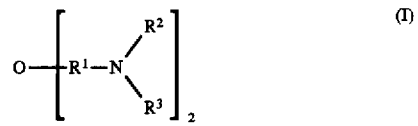

where $R^1$ is selected from the group consisting of an alkylene group; and
each of $R^2$ and $R^3$ is selected from the group consisting of an alkyl group.

2. A salt according to claim 1, wherein $R^1$ has no more than four carbon atoms.

3. A salt according to claim 1, wherein $R^2$ and $R^3$ each represent alkyl groups having no more than 8 carbon atoms.

4. A salt according to claim 3, wherein $R^2$ and $R^3$ together have no more than four carbon atoms.

5. A salt according to claim 1, wherein the diamino ether consists bis(2-dimethylaminoethyl) ether.

6. A process for preparing a clavulanic acid salt according to claim 1, which comprises reacting said diamino ether of formula (1) with clavulanic acid, or a salt thereof, in an organic solvent, and isolating the resulting salt.

7. A process for preparing a clavulanic acid salt according to claim 1, with substantially rosette type crystals, which process comprises preparing a substantially water free solution of clavulanic acid, or a salt thereof, in an organic solvent which solution is at a maintained temperature of between 0° and 15° C., and reacting said clavulanic acid, or salt thereof, with said diamino ether of formula (I) in said organic solvent.

8. A process according to claim 7, wherein the temperature of the solution is kept at less than 10° C.

9. A process according to claim 6, wherein the organic solvent is selected from the group consisting of an aliphatic carboxylic ester and a substantially water-immiscible aliphatic ketone.

10. A process according to claim 9, wherein said carboxylic ester is ethyl acetate.

11. A process according to claim 10, wherein said solvent further comprises a co-solvent.

12. A process according to claim 11, wherein said co-solvent is selected from the group consisting of acetone, acetonitrile and tetrahydrofuran.

13. A process according to claim 6, wherein the resulting salt is converted to a further pharmaceutically acceptable salt of clavulanic acid.

14. A process according to claim 13, wherein said further salt is the potassium salt.

15. A pharmaceutical composition comprising a pharmaceutically acceptable di-clavulanate salt acid according to claim 1 and a pharmaceutically acceptable carrier, diluent or excipient therefor.

16. A pharmaceutical composition according to claim 15, which further has a beta-lactam antibiotic.

17. A pharmaceutical composition according to claim 16, wherein said antibiotic is selected from the group consisting of penicillin and a cephalosporin.

* * * * *